US00PP23774P3

(12) United States Plant Patent
Meilland

(10) Patent No.: US PP23,774 P3
(45) Date of Patent: Jul. 30, 2013

(54) CLIMBING ROSE PLANT NAMED 'MEILACLOST'

(50) Latin Name: *Rosa hybrida*
Varietal Denomination: Meilaclost

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 369 days.

(21) Appl. No.: 13/064,224

(22) Filed: Mar. 11, 2011

(65) Prior Publication Data

US 2012/0233729 P1 Sep. 13, 2012

(51) Int. Cl.
*A01H 5/00* (2006.01)

(52) U.S. Cl.
USPC ..... Plt./111

(58) Field of Classification Search
USPC ..... Plt./111
See application file for complete search history.

(56) References Cited

U.S. PATENT DOCUMENTS

PP541 P * 8/1942 Brownell ..... Plt./111
PP16,611 P3 * 6/2006 Devor ..... Plt./111

OTHER PUBLICATIONS

Anonymous. 'MEIlaclost' Rose. Helpmefind.com available at http://helpmefind.com/gardening/1.php?1=2.63482.1&tab=1 accessed May 3, 2013.*
PLUTO UPOV Citations for 'Meilaclost' Accessed May 6, 2013.*

* cited by examiner

*Primary Examiner* — Wendy C Haas
(74) *Attorney, Agent, or Firm* — Buchanan Ingersoll & Rooney P.C.

(57) ABSTRACT

A new and distinct variety of rose plant is provided which commonly commences blooming early in the season and forms abundantly and substantially continuously attractive yellow semi-double blossoms that tend to be flattened cup-shaped when fully open. A very strong climbing growth habit is displayed. Attractive dense decorative green foliage is formed having a semi-glossy upper surface. No particular disease problem has been observed. The new variety is particularly well suited for providing attractive colorful ornamentation when grown in the landscape.

1 Drawing Sheet

Figures 1, 2, 3, 4, 5, 6, 7, 8, 9, 10, 11, 12, 13, 14, 15, 16, 17, 18:
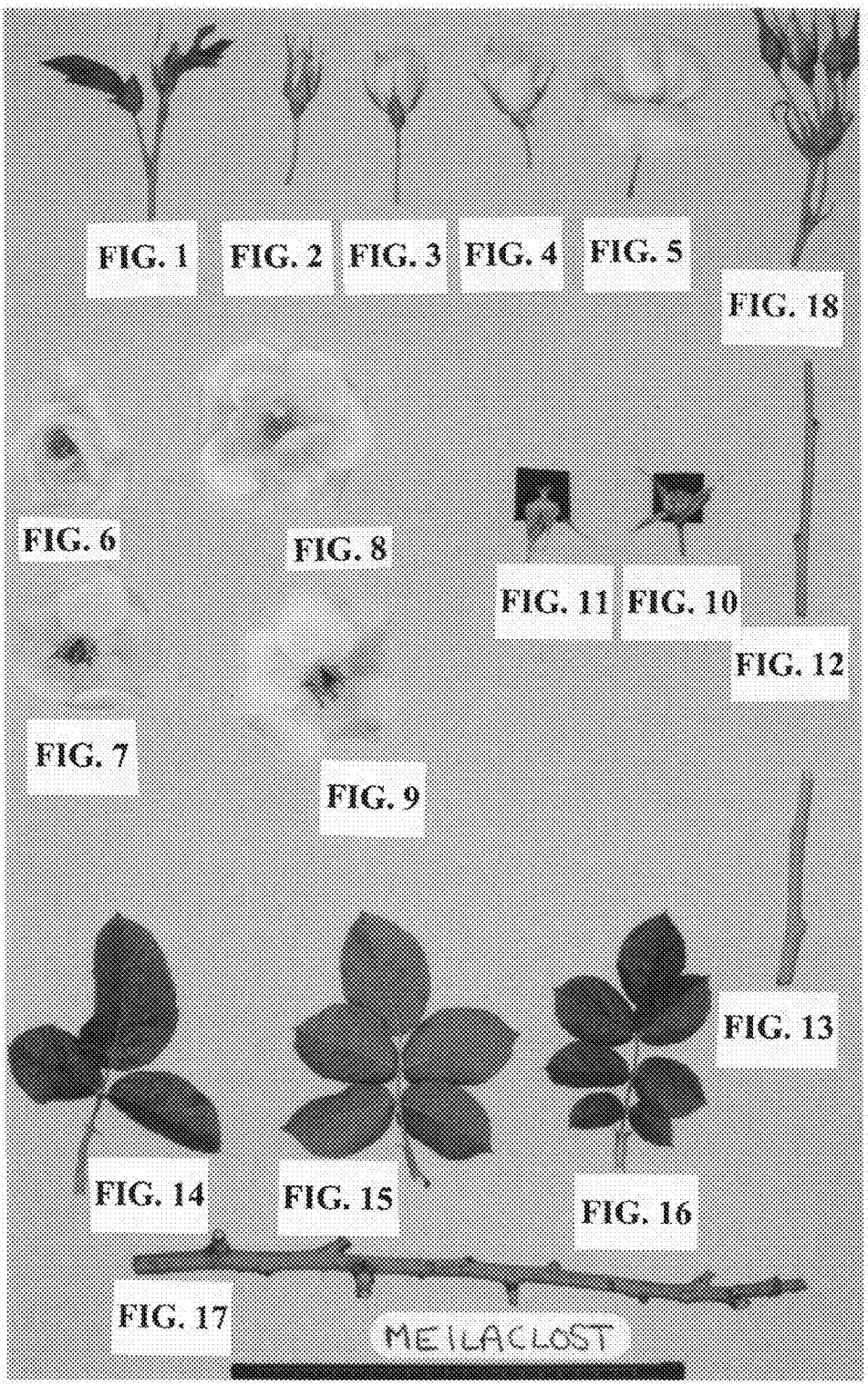

Botanical/commercial classification: *Rosa hybrida*/Climbing Rose Plant.
Varietal denomination: cv. Meilaclost.

SUMMARY OF THE INVENTION

The new variety of *Rosa hybrida* Climbing rose plant of the present invention was created at Le Cannet-Des-Maures, Var, France, by artificial pollination wherein two parents were crossed which previously had been studied in the hope that they would contribute the desired characteristics. The female parent (i.e., the seed parent) was the 'Deljaune' variety (non-patented in the United States). The male parent (i.e., the pollen parent) of the new variety was the 'Senateur Lafolette' variety (non-patented in the United States) The parentage of the new variety can be summarized as follows:

'Deljaune'×'Senateur Lafolette'.

The seeds resulting from the above pollination were sown and small plants were obtained which were physically and biologically different from each other. Selective study resulted in the identification of a single plant of the new variety.

It was found that the rose plant of the present invention possesses the following combination of characteristics:

(a) abundantly and substantially continuously forms attractive yellow semi-double blossoms that tend to be flattened cup-shaped when fully open,
(b) exhibits a very strong climbing growth habit, (c) forms dense decorative green foliage with a semi-glossy aspect on the upper surface, and
(d) is well suited for providing attractive colorful ornamentation when grown in the landscape.

The blooming tends to commence early in the season during observations to date. The bright yellow coloration of the blossoms contrasts nicely with the green foliage.

The new variety well meets the needs of the horticultural industry. It can be grown to advantage as an attractive Climber in parks, gardens, public areas, and in residential settings.

The new variety of the present invention can be readily distinguished from its ancestors, as well as other climbing rose varieties that are available to others for comparison. More specifically, the blossoms of the 'Deljaune' variety are medium yellow shaded with ochre in coloration, and the blossoms of the 'Senateur Lafolette' variety are orange to an orange blend in coloration.

The characteristics of the new variety have been found at Le Cannet-Des-Maures, Var, France, to be homogeneous and stable and to be strictly transmissible by asexual propagation, such as budding, grafting, and the rooting of cuttings, from one generation to another. Accordingly, the new variety reproduces in a true-to-type manner by such asexual propagation.

The new variety has been named 'Meilaclost'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during April while growing outdoors on *Rosa laxa* understock at LeCannet-des-Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower during the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates specimen of a leaf with five leaflets—plan view—under surface;

FIG. 16—illustrates a specimen of a leaf with seven leaflets—plan view—upper surface;

FIG. 17—illustrates a specimen of a principal branch; and

FIG. 18—illustrates a cluster of buds.

DETAILED DESCRIPTION

The chart used in the identification of colors is that of The Royal Horticultural Society (R.H.S. Colour Chart), London, England. The description is based on the observation of one-year-old specimens of the new variety during April while growing on *Rosa laxa* understock outdoors at Le Cannet-Des-Maures, Var, France.

Class: Climbing Rose.

Plant:

*Habit.*—Climbing.

Branches:

*Thorns.*—Size: commonly approximately 0.9 cm in length on average on adult stems. configuration: rather upright, very elongated and curved downwards on the upper surface, and slightly concave on the under surface with an obovate and longish base. quantity: commonly 7 on average over a length of 10 cm.

Leaves:

*Leaflet number.*—3, 5 (most often), and 7.

*Leaflet shape.*—Generally oval with somewhat cuspidate apex and a rounded base.

*Leaflet margins.*—Finely denticulate.

*Leaflet size.*—A terminal leaflet commonly is approximately 7.6 cm in length on average, and approximately 5 cm in width on average at the widest point.

*Overall appearance.*—Dense with a semi-glossy aspect on the upper surface.

*Color.*—Young leaves: upper surfaces commonly are near Green Group 139A, and under surfaces commonly are near Yellow-Green Group 147B.

*Stipules.*—Adnate, pectinate, rather broad, approximately 3 cm in length on average, approximately 0.6 cm in width on average, on the upper surface near Green Group 141B in coloration, and on the under surface near Yellow-Green Group 143A in coloration.

*Petiole.*—Glandular on the upper surface, and smooth on the under surface, approximately 6.4 cm in length on average for a terminal leaflet, on the upper surface near Green Group 141A in coloration, and on the under surface near Green Group 143B in coloration.

*Rachis.*—On the upper surface near Green Group 141A in coloration, and the under surface near Yellow-Green Group 143B in coloration.

Inflorescence:

*Bearing.*—Commonly in clusters of on average approximately 2 to 5 blossoms per stem.

*Peduncle.*—Tomentose, commonly approximately 5.7 cm in length on average, approximately 0.3 cm in diameter on average, and near Green Group 143B in coloration.

*Sepals.*—Shape: longish pointed, narrow, and generally upright at the base. length: commonly approximately 4.5 cm on average. width: commonly approximately 1.1 cm on average at the base. number: five. texture: the inner surface commonly is tomentose, and near Yellow-Green Group 146B in coloration, and the outer surface commonly is tomentose and near Green Group 143A in coloration.

*Buds.*—Shape: commonly elongated. length: as the calyx breaks commonly approximately 2.6 cm on average. diameter: as the calyx breaks commonly approximately 1.4 cm on average at the widest point. color (as the calyx breaks): upper surface: near Yellow Group 5A. under surface: near Yellow Group 6C.

*Flower.*—Form: semi-double. configuration: somewhat flattened cup-shaped when fully open. diameter: commonly approximately 13 cm on average when fully open. color (in course of opening): upper surface: near Yellow Group 3A. under surface: near Yellow Group 5B. color (open flower): upper surface: near Yellow Group 3C. under surface: near Yellow Group 5C. petal number: commonly approximately 15 to 18 on average under normal growing conditions. petal shape: commonly with a rounded tip and a rounded base. petal size: commonly approximately 6.4 cm in length on average, and approximately 6 cm in width on average. petal texture: firm and somewhat leathery. petal arrangement: imbricated and commonly without petaloids. fragrance: none. petal drop: good, with the petals commonly dropping cleanly and freely before drying. stamen number: commonly approximately 135 on average, and regularly arranged around the pistils. anthers: approximately 0.3 cm in size on average, and near Yellow-Orange Group 23B in coloration. filaments: commonly approximately 0.7 cm in length on average, and near Yellow Group 6A in coloration. pollen: present. pistils: commonly approximately 83 on average. styles: commonly approximately 1.1 cm in length on average, and near Yellow Group 2D in coloration. stigma: commonly approximately 0.1 cm in size on average, and near Yellow-Green Group 150D in coloration.

*Receptacle.*—Generally funnel-shaped in configuration, commonly approximately 0.7 cm in length on average, commonly approximately 1 cm in width at the widest point, commonly the surface is smooth, and the coloration commonly is near Green Group 143A.

Development:

*Vegetation.*—Very strong.

*Blossoming.*—Abundant and substantially continuous commonly beginning early in the season.

*Tolerance to diseases.*—Good, with no particular disease concerns having been encountered during observations to date.

The new 'Meilaclost' variety has not been observed under all possible environmental conditions to date. Accordingly, it is possible that the phenotypic expression may vary somewhat with changes in light intensity and duration, cultural practices, and other environmental conditions.

I claim:

1. A new and distinct rose plant characterized by the following combination of characteristics:

(a) abundantly and substantially continuously forms attractive yellow semi-double blossoms that tend to be flattened cup-shaped when fully open, (b) exhibits a very strong climbing growth habit, (c) forms dense decorative green foliage with a semi-glossy aspect on the upper surface, and (d) is well suited for providing attractive colorful ornamentation when grown in the landscape;

substantially as herein shown and described.

* * * * *

MEILACLOST